(12) United States Patent
Roulston

(10) Patent No.: US 9,688,950 B2
(45) Date of Patent: Jun. 27, 2017

(54) PHOTOBIOREACTOR FOR LIQUID CULTURES

(71) Applicant: Industrial Plankton Inc., Victoria (CA)

(72) Inventor: Robert Roulston, Victoria (CA)

(73) Assignee: INDUSTRIAL PLANKTON INC., Victoria (CA)

( * ) Notice: Subject to any disclaimer, the term of this patent is extended or adjusted under 35 U.S.C. 154(b) by 15 days.

(21) Appl. No.: 14/410,195

(22) PCT Filed: Jun. 30, 2013

(86) PCT No.: PCT/IB2013/055369
§ 371 (c)(1),
(2) Date: Dec. 22, 2014

(87) PCT Pub. No.: WO2014/006551
PCT Pub. Date: Jan. 9, 2014

(65) Prior Publication Data
US 2015/0299630 A1 Oct. 22, 2015

(51) Int. Cl.
*C12M 1/00* (2006.01)
*C12M 3/00* (2006.01)
(Continued)

(52) U.S. Cl.
CPC ............ *C12M 21/02* (2013.01); *C12M 23/22* (2013.01); *C12M 23/38* (2013.01); *C12M 29/00* (2013.01);
(Continued)

(58) Field of Classification Search
CPC ...... C12M 21/02; C12M 31/10; C12M 31/02; C12M 31/08; C12M 23/06; C12M 43/06;
(Continued)

(56) References Cited

U.S. PATENT DOCUMENTS 5,137,828 A * 8/1992 Robinson ............... C12M 21/02
435/292.1
5,585,266 A * 12/1996 Plitt ...................... C12M 23/52
210/150

(Continued)

FOREIGN PATENT DOCUMENTS

CN 101701180 A 5/2010
JP 03087171 A 4/1991
(Continued)

OTHER PUBLICATIONS

Supplementary European Search Report, EP13812910. Feb. 4, 2016, 3pp.
(Continued)

*Primary Examiner* — Michael Hobbs
(74) *Attorney, Agent, or Firm* — Perry + Currier Inc.

(57) ABSTRACT

A bioreactor for culturing cells in a liquid environment is provided that is designed to reduce the chance of contamination, contain the contamination should it occur, and readily clean and sterilize all or part of the bioreactor in response to contamination, or on a schedule. A processor-controlled method of promoting sterility in a bioreactor is also provided.

8 Claims, 10 Drawing Sheets

(51) Int. Cl.
*C12M 1/12* (2006.01)
*C12M 1/36* (2006.01)
*C12M 1/26* (2006.01)
*C12M 1/34* (2006.01)

(52) U.S. Cl.
CPC ............ *C12M 29/06* (2013.01); *C12M 31/08* (2013.01); *C12M 33/00* (2013.01); *C12M 37/00* (2013.01); *C12M 39/00* (2013.01); *C12M 41/00* (2013.01); *C12M 41/48* (2013.01)

(58) Field of Classification Search
CPC .......... C12M 31/12; A01G 33/00; C12N 1/12; C02F 3/32
USPC ...................................................... 435/292.1
See application file for complete search history.

(56) References Cited

U.S. PATENT DOCUMENTS

| | | |
|---|---|---|
| 6,509,188 B1 | 1/2003 | Trosch et al. |
| 2005/0208473 A1 | 9/2005 | Krichevsky |
| 2009/0023199 A1* | 1/2009 | Gal ........................ C12M 21/02 435/286.5 |
| 2011/0111489 A1 | 5/2011 | Beese |
| 2011/0136225 A1 | 6/2011 | Vunjak-Novakovic |
| 2012/0208254 A1* | 8/2012 | Smith .................... C12M 21/02 435/167 |

FOREIGN PATENT DOCUMENTS

| | | |
|---|---|---|
| JP | 2012525842 A * | 10/2012 |
| WO | WO2006/071716 A2 | 7/2006 |

OTHER PUBLICATIONS

Database WPI, Week 201033, Thomson Scientific, London, GB AN 2010-F20363.
WIPO, Canadian International Searching Authority, International Search Report mailed Oct. 11, 2013, International Patent Application No. PCT/IB2013/055369, 4 Pages.
WIPO, Canadian International Searching Authority, Written Opinion of the International Searching Authority mailed Oct. 11, 2013, International Patent Application No. PCT/IB2013/055369, 4 Pages.
Notice of Reasons for Rejection and its English Translation dated Feb. 14, 2017 for Japanese Patent Application No. 2015-519465.

* cited by examiner

PHOTOBIOREACTOR FOR LIQUID CULTURES

FIELD

The present technology relates to a system for scale up and steady state production of liquid cultures under sterile conditions. More specifically, the technology relates to a safe bioreactor system for growing aquatic biological materials including salt water zooplankton and phytoplankton and combinations thereof.

BACKGROUND

Bioreactors have been used for many years for cell culture, most notably for fermentation and more recently for the growth of bacteria. These cultures are usually contained in stainless steel vessels where gas exchange, temperature, pH, dissolved oxygen levels, and circulation are closely monitored and controlled.

Photobioreactors are reactors for material that requires light. There are many designs, ranging from open-air races, to tubes, to transparent vessels. The vessels may have banks of lights around the periphery or a central core of lights. The level of control ranges from essentially none, to strict monitoring of the growth conditions. Where there is no control over the growth conditions, sterility and maintenance of cell culture purity are not considered. This may be adequate for growth of algae for biofuel production, but is not for the growth of algae as a food source. In this instance, sensors and controls, as disclosed in US Publication No. 20110136225, are employed. A bioreactor module can be connected to one or more functional modules such as a pump module, a stimulation signal generation module, a motor module, a mechanical transmission module, a gas exchange module, a temperature module, a humidity module and/or a $CO_2$ module, among others. The bioreactor and functional modules can include standard or universal connectors to facilitate connection and movement of modules. The bioreactor system can be controlled and/or monitored by a controller that can individually identify and control each connected module and that can be adapted to collect signal data from sensors embedded in any of the modules.

The use of sensors may require special adaptations. As disclosed in US Publication No. 20110111489, a sensor adapter comprises an accommodating channel, in which the sensor can be positioned and the one end region of which is closed off by a semipermeable membrane. Moreover, the sensor adapter comprises a hollow cylindrical sealing structure, which is disposed within the accommodating channel coaxially with the longitudinal axis of the latter and with which the sensor can be disposed gas tight adjacent to the semipermeable membrane.

Processors and programmes can be used to monitor outputs from sensors and run the various controllers. As disclosed in US Publication No. 20050208473, decision making software can be used that utilizes detected changes in the course of fermentation. Decisions are aimed at determining the optima for cellular growth, optimizing for production or degradation of metabolites or substrates, or determining the limits of growth under various combinations of conditions. The invention determines optima or limits in a manner more quickly and at less cost than traditional methods. The basis for the computer generated decisions may be first or second derivative changes observed such as inflection points, limits on allowable rates of change, or the like. The most common measured parameter controlling the decision making process is the optically observed growth of the cells (e.g. microbial, animal, or plant cell cultures) under study. Any other measurable parameter (e.g. pH, temperature, pigment production) may be used to control the process (i.e., the independent variable). This process and variations of this process on a laboratory scale are valuable for research and development, education, pilot plant models, and biomanufacturing optimization, including scale up to production volumes.

SUMMARY

The present technology is an integrated bioreactor comprising air, carbon dioxide, nutrient, sterilizant and neutralizer sources, lines from the sources to at least one culture vessel, a culture line for delivering seed culture to the vessel, a manifold to direct flow to and from the culture vessel, lights, sensors and a processor to control the functions of the bioreactor.

In one embodiment, the bioreactor has an integrated sterilization system for in situ sterilization. The technology allows for regular automated cleaning and sterilizing of a bioreactor with minimal interruption in production. Downtime can be less than 1 hour each week. From one to a plurality of culture vessels make up the bioreactor. The bioreactor provides controlled, closed scale up.

Specifically, the bioreactor, which is for culturing cells in a liquid environment, comprises:

culture lines, culture medium lines, and a combined gas and sterilizant manifold, the lines and manifold comprising valves to control flow direction and flow rates, optionally, pressure relief valves to relieve pressure and optionally, pumps to maintain pressure;

a source of pressurized carbon dioxide, a source of pressurized air and a sterilizant source each in communication with the manifold;

a culture medium source in liquid communication with the culture medium lines;

at least one vessel, the vessel comprising a side wall, a lid, a bottom, sensors for reporting culture conditions, a sparger, a sprayer, an inlet and an outlet;

a transfer system for accepting a seed culture container, the transfer system in communication with a first vessel;

and a processor programmed to control culture conditions, execution of sterilization schedules, and incremental increases of volume of a culture on a schedule.

For use with phototrophic or mixotrophic cultures, at least the side wall is light transmitting and the vessels are provided with lighting proximate the side wall.

The bioreactor may further comprise a base, wherein the side wall comprises substantially vertical contours and the base is contoured to mate with the side wall.

The vessels may further be provided with reflectors proximate the lighting.

The bioreactor may further comprise at least one cleaner, the cleaner comprising a blade, an arm and a drive, the blade located within the at least one vessel and magnetically coupled to the arm, or directly driven, the arm configured to rotate around the vessel, and the drive for driving rotation of the arm, such that in use, the blade wipes the side walls within the vessel.

The sterilizant source may be a steam boiler or a liquid sterilizant pack.

The processor may be programmed to increase culture volume on a cell density based schedule.

The bioreactor may comprise at least two vessels, wherein the processor is programmed to transfer the culture from a first vessel to a second vessel to increase culture volume.

The bioreactor may comprise one vessel, wherein the processor is programmed to add culture medium to the vessel to increase culture volume.

In another embodiment, a bioreactor is provided, the bioreactor comprising:

culture lines, culture medium lines, and gas lines, the lines comprising valves and optionally, pumps;

gas sources in gaseous communication with the gas lines;

a culture medium source in liquid communication with the culture medium lines;

at least one culture vessel comprising a side wall, a lid, a bottom, sensors for reporting culture conditions, a gas sparger in communication with the gas line, a culture medium sprayer in communication with the culture medium line, a culture inlet and a culture outlet;

a pressure driven transfer system for transferring a culture from a seed culture container to the culture vessel;

and a processor programmed to control culture conditions, incremental increases in culture volume and execution of sterilization cycles, the improvement being an integrated sterilization system for in situ sterilization of the bioreactor.

The integrated sterilization system may comprise the gas lines, a sterilizant source in communication with the gas lines, and sterilization cycle protocols programmed in the processor.

The sterilizant source may be a steam boiler.

The sterilizant source may be a sterilizing fluid pack.

The bioreactor may further comprise a cleaner, the cleaner comprising a blade, an arm and a drive, the blade located within the vessel and coupled to the arm, the arm configured to rotate and the drive for driving rotation of the arm, such that in use, the blade wipes the side walls within the vessel.

At least the side wall may be light transmitting, and the vessels may be provided with lighting proximate the side wall.

A bioreactor vessel is also provided, the vessel comprising a side wall, a lid, a bottom, a base, the base contoured to mate with the side wall, sensors for reporting culture conditions, a gas sparger for communication with a gas line, a culture medium sprayer for communication with a culture medium line, a culture inlet and a culture outlet, wherein the side wall is light-transmitting and comprises substantially vertical contours of peaks and valleys.

The bioreactor vessel may further comprise a layer proximate the lighting, the vertical contours and layer defining air channels.

The bioreactor vessel may further comprise a combined stand and cooling system, the combined stand and cooling system comprising a framework of conduits and at least one blower, the blower in gaseous communication with a conduit inlet, the frame work of conduits having a series of outlets aligned with the air channels, such that in use, air is blown into a lower end of the channels and rises to the top of the channels thereby cooling the bioreactor vessel.

A processor-controlled method of promoting sterility in a bioreactor is also provided, the bioreactor comprising at least two culture vessels, sensors, culture lines, culture medium lines, a combined gas and sterilizant manifold, a sterilizant source, and inline filters between the ambient environment and the bioreactor, and a processor, the method comprising:

the processor signaling a start of the sterilizing cycle;

delivering sterilizant through the manifold to the bioreactor, at least downstream of the inline filters;

and signaling an end of the sterilizing cycle, thereby promoting sterility in the bioreactor.

The method may further comprise sensing contamination, and the processor signaling emptying of a culture vessels prior to signaling the start of the sterilization cycle.

The method may further comprise a cleaning step prior to signaling the start of the sterilization cycle.

A processor controlled method of culturing plant cells in a bioreactor is also provided, the bioreactor comprising a processor, a sterilizable transfer valve for accepting a seed culture container, at least one culture vessel with a culture line inlet and a culture line outlet, sensors for the culture vessel, lights, culture lines between the transfer valve and the at least one culture vessel, culture medium lines, a combined gas and sterilizant manifold, a sterilizant source, and inline filters between the ambient environment and the bioreactor, the method comprising:

i) attaching the seed culture container to the transfer valve;

ii) the processor signaling a start of the sterilizing cycle, controlling delivering sterilizant through the manifold to the bioreactor, at least downstream of the inline filters, then signaling a stop of the sterilizing cycle;

iii) the processor signaling opening of the transfer valve and signaling opening of the culture medium lines, thereby controlling delivering culture medium and culture to a first vessel;

iv) the sensors sending culture condition data to the processor, the processor controlling culture conditions; and v) the processor terminating culturing and signaling emptying of the first culture vessel.

The method may further comprise:

vi) the processor signaling cleaning of the at least one culture vessel.

The method may further comprise:

vii) the processor controlling transferring the emptied culture to at second culture vessel and signaling opening of the culture medium lines, thereby filling the second culture vessel.

The method may further comprise:

viii) the processor signaling cleaning of the culture vessels.

In another embodiment, a bioreactor for culturing cells in a liquid environment is provided, the bioreactor comprising:

culture lines, culture medium lines, and a combined gas and sterilizant manifold, the lines and manifold comprising valves to control flow direction and flow rates, optional pressure release valves to relieve pressure and optionally, pumps to maintain pressure;

a culture vessel, the vessel comprising a transparent side wall, wherein the side wall comprises substantially vertical contours, a base, the base contoured to mate with the side wall, a lid, sensors for reporting culture conditions, a sparger, a sprayer, an inlet and an outlet;

a light source disposed around the side wall;

and a processor programmed to control culture conditions and execution of sterilization schedules.

The side wall contours may be ridges and valleys, the peak to valley height about $1/16$th of an inch to about 12 inches and the distance between the peaks about $1/16$th of an inch to about 12 inches.

The peak to valley height may be about 1 inch to about 6 inches and the distance between the peaks may be about 1 inch to about 6 inches.

The bioreactor may further comprise a cooling system, the cooling system comprising at least one fan and a distribution plate in communication with the at least one fan, the distribution plate having a network for directing air flow into each valley.

The bioreactor may further comprise a cooling plate or a cooling water jacket disposed beneath the distribution plate and for communication with a refrigeration source.

The bioreactor may further comprise a source of pressurized carbon dioxide, a source of pressurized air and a sterilizant source each in gaseous communication with the manifold.

A processor-controlled method of promoting sterility in a bioreactor is also provided, the bioreactor comprising:
culture lines, culture medium lines, and gas lines, the lines comprising valves and optionally, pumps;
gas sources in gaseous communication with the gas lines;
a culture medium source in liquid communication with the culture medium lines;
at least one culture vessel comprising a side wall, a lid, a bottom, sensors for reporting culture conditions, a gas sparger in communication with the gas line, a culture medium sprayer in communication with the culture medium line, a culture inlet and a culture outlet;
a pressure driven transfer system for transferring a culture from a seed culture container to the culture vessel;
a processor; and
an integrated sterilization system for in situ sterilization of the bioreactor,
the method comprising:
the processor signaling a start of the sterilizing cycle;
delivering sterilant through the integrated sterilization system of the bioreactor, at least downstream of the inline filters; and
the processor signaling an end of the sterilizing cycle, thereby promoting sterility in the bioreactor.

The method may further comprise the sensors reporting data to the processor, the processor determining contamination, and the processor signaling emptying of a culture vessels prior to signaling the start of the sterilization cycle.

The method may further comprise a cleaning step prior to signaling the start of the sterilization cycle.

A processor-controlled method of promoting sterility in a bioreactor is also provided, the bioreactor comprising:
culture lines, culture medium lines, and a combined gas and sterilizant manifold, the lines and manifold comprising valves to control flow direction and flow rates, optional pressure release valves to relieve pressure and optionally, pumps to maintain pressure;
a culture vessel, the vessel comprising a transparent side wall, wherein the side wall comprises substantially vertical contours, a base, the base contoured to mate with the side wall, a lid, sensors for reporting culture conditions, a sparger, a sprayer, an inlet and an outlet;
a light source disposed around the side wall;
and
a processor programmed to control culture conditions and execution of sterilization schedules.
the method comprising:
the processor signaling a start of the sterilizing cycle;
delivering sterilant through the combined gas and sterilizant manifold, at least downstream of the inline filters; and
signaling an end of the sterilizing cycle, thereby promoting sterility in the bioreactor.

The method may further comprising the sensors reporting data to the processor, the processor determining contamination, and the processor signaling emptying of a culture vessels prior to signaling the start of the sterilization cycle.

The method may further comprise a cleaning step prior to signaling the start of the sterilization cycle.

A processor controlled method of culturing plant cells in a bioreactor is also provided, the bioreactor comprising:
culture lines, culture medium lines, and gas lines, the lines comprising valves and optionally, pumps;
gas sources in gaseous communication with the gas lines;
a culture medium source in liquid communication with the culture medium lines;
at least one culture vessel comprising a side wall, a lid, a bottom, sensors for reporting culture conditions, a gas sparger in communication with the gas line, a culture medium sprayer in communication with the culture medium line, a culture inlet and a culture outlet;
a pressure driven transfer system for transferring a culture from a seed culture container to the culture vessel;
a processor programmed to control culture conditions, incremental increases of culture volume and execution of sterilization cycles; and
an integrated sterilization system for in situ sterilization of the bioreactor,
the method comprising:
i) attaching the seed culture container to a first culture line;
ii) the processor signaling pressurizing the seed culture container to deliver culture to the culture vessel;
iii) the processor signaling opening of the culture medium lines, thereby controlling delivering culture medium to the culture vessel;
iv) the sensors sending culture condition data to the processor, the processor controlling culture conditions and controlling incremental increases in culture volume in the culture vessel; and
v) the processor terminating culturing and signaling emptying of the culture vessel.

The method may further comprise:
vi) the processor signaling cleaning of the culture vessel.

The method may further comprise:
vii) the processor signaling execution of the sterilization cycle.

In another embodiment a bioreactor for culturing cells in a liquid environment is provided, the bioreactor comprising:
culture lines, culture medium lines, and a combined gas and culture manifold, the lines and manifold comprising valves to control flow direction and flow rates, pressure relief valves to relieve pressure and pumps to maintain pressure;
a source of pressurized carbon dioxide and a source of pressurized air in communication with the manifold;
a culture medium source in liquid communication with the culture medium lines;
at least one vessel, the vessel comprising a side wall, a lid, a bottom, sensors for reporting culture conditions, a sparger, at least one inlet and an outlet;
a sterilizant source in communication with the vessel;
a transfer system for accepting a seed culture container, the transfer system in communication with a first vessel;
and
a processor programmed to control culture conditions, execution of sterilization schedules, and incremental increases of volume of a culture on a schedule.

For phototrophic or mixotrophic cultures, at least the side wall may be light transmitting and the vessels may be provided with lighting proximate the side wall.

The bioreactor may further comprise a base, wherein the side wall comprises substantially vertical contours and the base is contoured to mate with the side wall.

The vessels may be further provided with reflectors proximate the lighting.

The bioreactor may further comprise at least one cleaner, the cleaner comprising a blade, an arm and a drive, the blade located within the at least one vessel and magnetically coupled to the arm, or directly driven, the arm configured to rotate around the vessel, and the drive for driving rotation of the arm, such that in use, the blade wipes the side walls within the vessel.

The sterilizant source may be a steam boiler or a liquid sterilizant pack.

The processor may be programmed to increase culture volume on a cell density based schedule.

The bioreactor may comprise at least two vessels, wherein the processor is programmed to transfer the culture from a first vessel to a second vessel to increase culture volume.

The bioreactor may comprise one vessel, wherein the processor is programmed to add culture medium to the vessel to increase culture volume.

The bioreactor may further comprise a heat exchanger or water jacket for cooling the culture vessel.

DESCRIPTION

Figure 1:
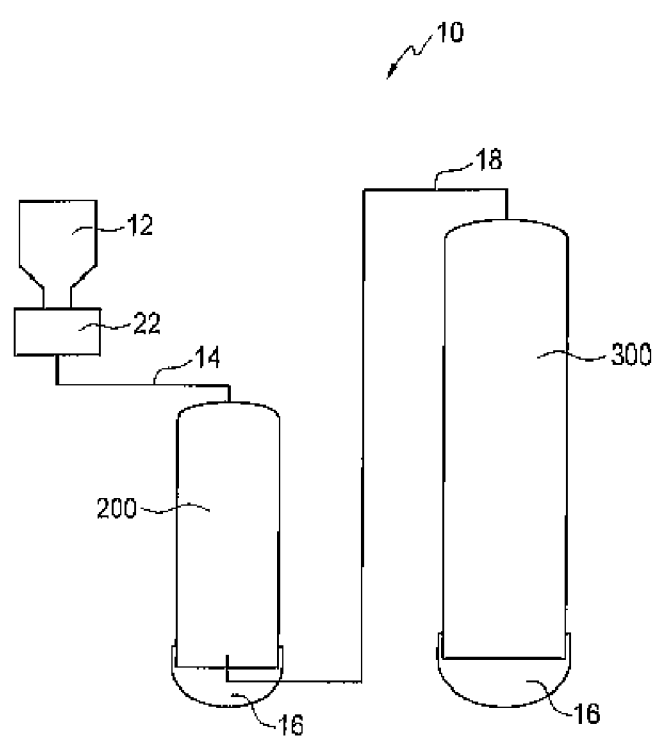
FIG. 1 is a plan view of the bioreactor of the present technology.

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting.

Further, The terms "comprising," "having," "including," and "containing" are to be construed as open-ended terms (i.e., meaning "including, but not limited to,") unless otherwise noted.

To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Definitions:

Aquatic—in the context of the present technology, aquaculture includes the culturing of biological material in fresh water, salt water, brackish water, brine and the like—essentially any liquid.

Culture—in the context of the present technology, culture, as in culture line or culture vessel, refers to a combination of biological material, culture medium and any additional chemicals produced by the biological material during the culturing process. Cultures require appropriate sources of food and energy, provided by the culture medium, and a suitable physical environment. Tissue cultures can themselves become a culture medium for viruses, which grow only with live cells. Cultures of only one kind of cells are known as pure cultures, as distinguished from mixed or contaminated cultures.

Cell—in the context of the present technology, cell means any cell or cells, as well as viruses or any other particles having a microscopic size, e.g. a size that is similar to that of a biological cell, and includes any prokaryotic or eukaryotic cell, for example, but not limited to bacteria, fungi, plant and animal cells. A cell may be living or dead. As used herein, a cell is generally living unless otherwise indicated. Cells may be a plurality of individual cells or may be cell clumps, aggregates or groupings. The cells may be undifferentiated or differentiated, but are not formed into tissues.

Tissue—in the context of the present technology, tissue means an aggregation of cells more or less similar morphologically and functionally.

Sensor—in the context of the present technology, sensor is defined as any device that can measure a measurable quantity. For examples, a sensor can be, but is not limited to a thermal detector, an electrical detector, a chemical detector, an optical detector, an ion detector, a biological detector, an electrochemical detector, a magnetic detector, a capacitive detector, a pressure detector, an ultrasonic detector, an infrared detector, a microwave motion detector, an electric eye, and an image sensor.

Culture medium—in the context of the present technology, culture medium refers to a liquid comprising chemicals needed to support growth and maintenance of cells. The chemicals may be nutrients, including but not limited to vitamins, minerals, micronutrients, amino acids. The chemicals may also comprise osmoticum, a carbon source, biological extracts, and buffers. A medium can be provided with one or more analytes to be consumed by one or more cells. In some instances, culture medium may simply be salt water, wherein salt water is defined as ocean water or brine pond water, or it may be brackish water.

Plant—in the context of the present technology, plant refers to any organism, cell or cells that photosynthesize.

Apparatus:

Itemized list of the main components:
1. Sterilizant system;
2. Water treatment system;
3. Clean-in-place system (CIP);
4. Air and CO2 addition;
5. Control system—Programmable Logic Controller (PLC) Based;
6. Seed culture container;
7. Scale up vessel;
8. Feed vessel; and
9. Cooling system (as described in "Second embodiment")

A bioreactor, generally referred to as 10, is shown in FIG. 1. A seed culture container 12 connects via a first culture line 14 to a scale up vessel 200, which in turn connects via a second culture line 18 to a feed vessel 300. The seed culture container 12 is transiently attached to the first culture line 14 via a sterilizable transfer valve 22, or alternatively, is directly attached to the scale up vessel 200 via the transfer valve 22, again transiently. There is an incremental volume increase in the vessels from the seed culture container 12 to the scale up vessel 200 to the feed vessel 300. Each vessel has a second bottom 16 to define a water chamber for cooling the vessels 200, 300. This functions as a heat exchanger.

Figure 2:
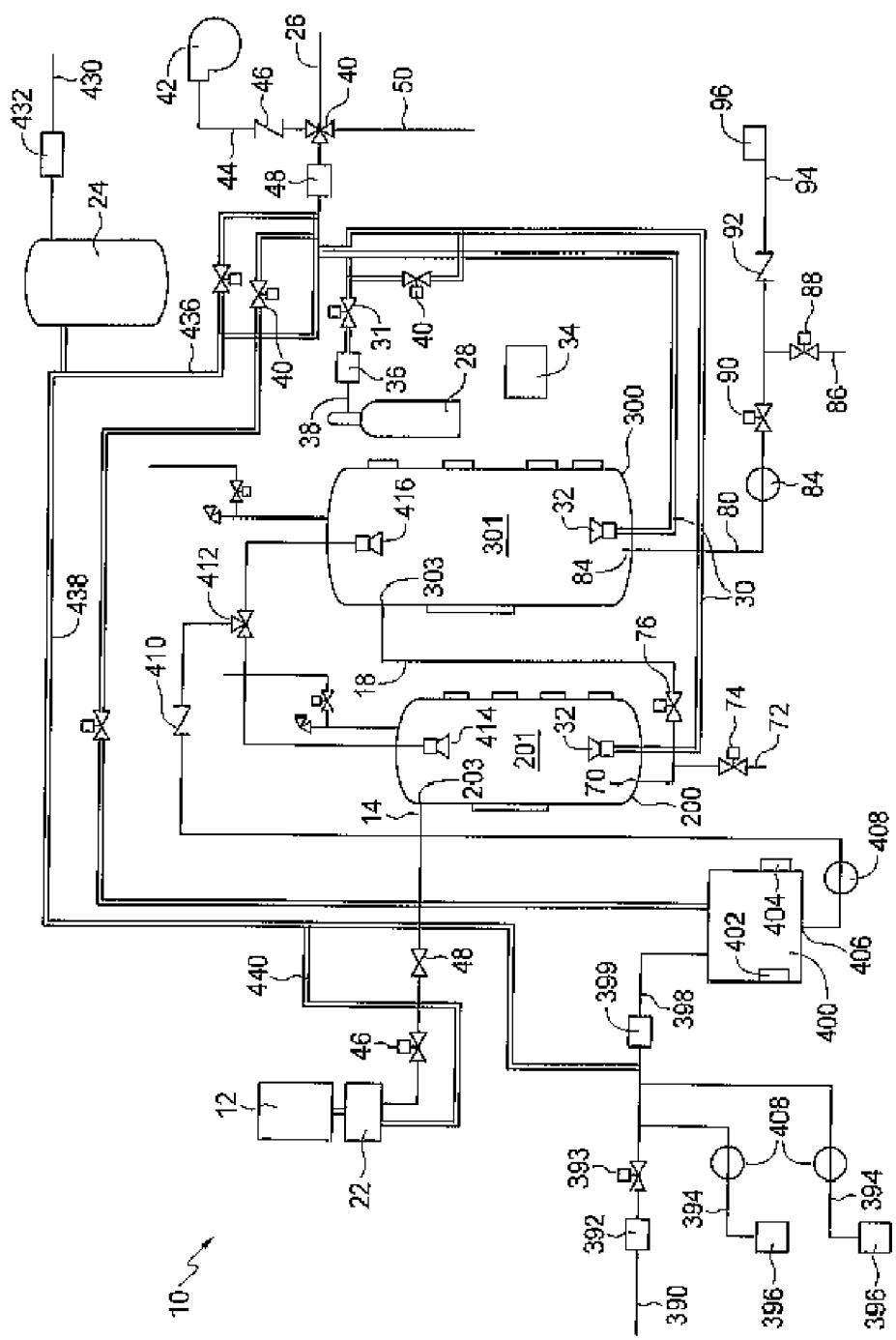
FIG. 2 is a schematic of the bioreactor of FIG. 1.

FIG. 2 is a schematic of the bioreactor 10. A steam generator 24 is used for sterilizing the bioreactor 10. An air source 26, which may be a tank or ambient air and a pressurized CO2 tank 28 are connected via gas lines 30 to the injectors 32 located in the interior 201 of the scale up vessel 200 and the interior 301 of the feeder vessel 300. A processor 34 controls delivery of air and CO2 as needed. A regulator and digital pressure gauge 36 is located downstream from the CO2 tank 28 on the CO2 line 38 portion of the gas line 30. A valve 31 is located downstream. Three way, 2 position solenoid valves 40 communicate with the processor 34 and are located on the gas lines 30. An air pump 42 is on the air line 44 portion of the gas line 30 and is calibrated to produce a pressure between about 2 psi to about 15 psi. A check valve 46 is located between the air pump 42 and one of the three way, two position solenoid valves 40. A 0.1 µm steam-in-place filter 48 is located upstream from the solenoid valve 40. The solenoid valve 40 splits the air line 44 into an air dump line 50 and the air line 44. The CO2 line 38 and the air line 44 connect at three way solenoid valves 40 to form the gas lines 30. The CO2 line 38, the air line 44, and the gas lines 30 form a manifold. This manifold also distributes steam or more generally, sterilizant, allowing for easy steam sterilization of the lines.

The first culture line 14 enters the scale up vessel 200 at an inlet 203. Downstream from the transfer valve 22, the first culture line 14 has a three way valve 430 that can be manually operated and a two way valve 432 in line. The first culture line 14 optionally has an inline pump to pressurize the transfer mechanism.

The second culture line 18 leaves the scale up vessel through an outlet 70. A first dump line splits 72 from the second culture line 18. Both have two way valves—74 on the dump line and 76 on the second culture line 18. The second culture line 18 enters the feed vessel 300 at an inlet 301.

A third culture line 80 leaves the feed vessel 300 through an outlet 82. The third culture line 80 passes through an inline pump 84, which is preferably a peristaltic pump or a shuttle pump, but may be a rotary pump, and a second dump line 86 splits off. Both have two way valves—88 on the dump line 86 and 90 on the third culture line 80. Additionally, the third culture line 80 has a one way check valve 92 downstream. An outlet 94 terminates the third culture line 80. At this point the feed culture is supplied to the customer either as is, or in a concentrated form, by including a concentrator 96 either upstream or downstream from the outlet 94. The concentrator 96 may be any suitable concentrator, for example, but not limited to a centrifuge or a filtration system.

A water line 390 for sea water has an inline 100 µm filter 392, is joined by two nutrient lines 394 from nutrient packs 396 to become a culture medium line 398 and then passes an ultravoilet (UV) light source 399 located downstream. The culture medium line 398 enters a booster tank 400 that is supplied with a heater 402 and a pressure sensor 404. The line 398 leaves the tank 400 through an outlet 406, passes through an inline pump 408, which is preferably a peristaltic pump or shuttle pump, but may be a rotary pump, and a one way check valve 410 to a three way diverter valve 412 that directs flow to the scale up vessel 200 or the feed vessel 300. A first sprayer 414 sprays the contents of the line into the scale up vessel 200. A second sprayer 416 sprays the contents of the line into the feed vessel 300. The sprayers 414 and 416 are preferably rotary spray nozzles. The processor 34 controls the one way check valve 410 and the three way diverter valve 412, which are solenoid valves, to control flow.

A fresh water supply 430 passes through a 50 µm filter 432 and enters a steam generator, for example, a boiler 434. A first steam line 436 from the steam generator 434 enters the CO2 line 38 and the air line 44 at the solenoid valves 40. A second steam line 438 enters the water line downstream from the nutrient lines 394 and upstream from the UV light source 399. A third steam line 440 delivers steam to the transfer valve 22. The steam lines, manifold and overall integration of the bioreactor allow for in situ sterilization of either the entire bioreactor, or select vessels and lines.

Figure 3:
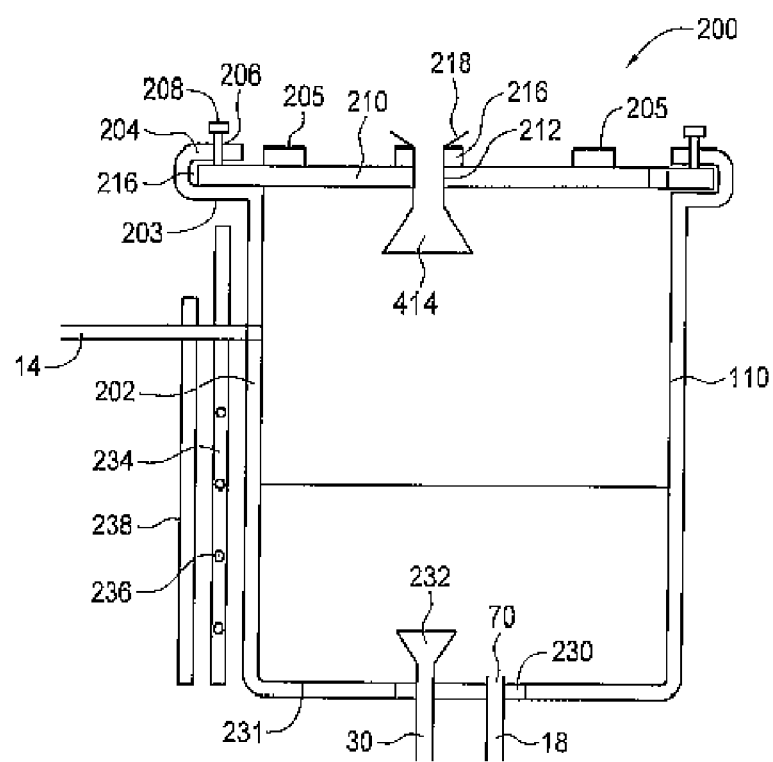
FIG. 3 is a longitudinal sectional view of the scale up vessel of the present technology.

The scale up vessel, generally referred to as 200 is shown in FIG. 3. The scale up vessel is about 200 to about 2,000 liters, or about 500 to about 1500 liters or 1,000 liters and all ranges therebetween. If algae or other plant material is to be cultured, at least the side walls 202 are transparent or light transmitting. The lip 203 of the wall 202 is formed into a flange 204 and has openings 206 to accept bolts 208 for affixing an airtight lid 210. As the vessel is steam-cleaned, both the vessel 200 and the lid 210 are made of steam-resistant material, for example, but not limited to fiberglass or a heat resistant polyethylene such as Tyvar®. The lid 210 has an access port 212 for accepting a clean in place system(CIP), generally referred to as 214. Gaskets 216 are located between the lid 210 and flange 204 and between a CIP flange 218 of the CIP 414 and the lid 210.

The scale up vessel 200 is equipped with a bottom access 230 on or in the vicinity of the bottom 231 connected to the gas lines 30 and the outlet 70 connected to the second culture line 18. The gas line 30 terminates in a sparger 232. The first culture line 14 enters into the scale up vessel 200 on a side wall 202. An optional thin plastic polymer shell 234 surrounds the side wall 202 and is equipped with light emitting diode grow lights 236. An optional reflective surface 238 is located on an outer side of the shell 234. Lights 205 may additionally be provided on the lid 210. As shown in FIG. 2, the scale up vessel 200 is provided with sensors for reporting culture conditions, for example, but not limited to each of a pH 240, optical density 242, temperature 244, and pressure sensor 246. Capacitance sensors 248 are located at a number of depths, for example, two located at ⅓ and ⅔ depth, three located at ¼, ½, ¾ depth or four located at ⅕, ⅖, ⅗ and ⅘ depth.

Figure 4:
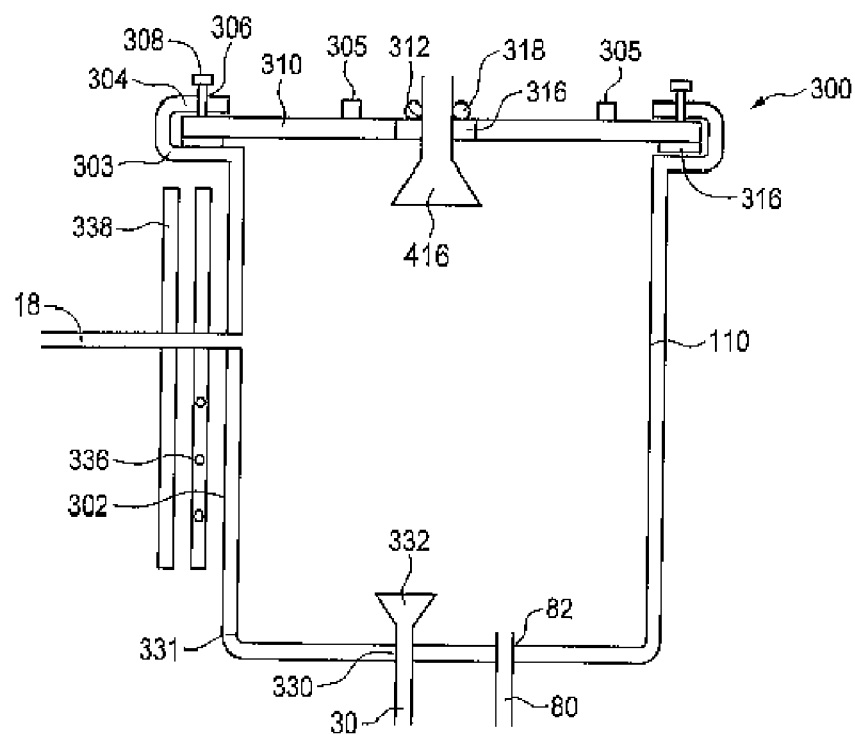
FIG. 4 is a longitudinal sectional view of the feed vessel of the present technology.

The feed culture vessel, generally referred to as 300, is shown in FIG. 4. The feed culture vessel is about 100 to about 100,000 liters, or about 250 to about 75,000 liters or 50,000 liters and all ranges therebetween. If algae or other plant material is to be cultured, at least the side walls 302 are transparent or light transmitting. The lip of the wall 303 is formed into a flange 304 and has openings 306 to accept bolts 308 for affixing an airtight lid 310. As the vessel is steam-cleaned, both the vessel 300 and the lid 310 are made of steam-resistant material, for example, but not limited to fiberglass or a heat resistant polyethylene such as Tyvar®. The lid 310 has an access port 312 for accepting a clean in place system (CIP), generally referred to as 416. Gaskets 316 are located between the lid 310 and flange 304 and between a CIP flange 318 and the lid 310.

The feed culture vessel 300 is equipped with a bottom access 330 on or in the vicinity of the bottom 331 connected to the gas lines 30 and an outlet 82 connected to the third culture line 80. The gas line 30 terminates in a sparger 332. The second culture line 18 enters the feed culture vessel 300 at a side wall 302. An optional thin plastic polymer shell 334 surrounds the vessel 300 and is equipped with light emitting diode grow lights 336. An optional reflective surface 338 is located on an outer side of the shell 334. Lights 305 may additionally be provided on the lid 310. As shown in FIG. 2, the feed culture vessel 300 is provided with sensors for reporting culture conditions, for example, but not limited to each of a pH 340, optical density 342, temperature 344, and pressure sensor 346. Capacitance sensors 348 are located at a number of depths, for example, two located at ⅓ and ⅔ depth, three located at ¼, ½, ¾ depth or four located at ⅕, ⅖, ⅗ and ⅘ depth.

The bioreactor is controlled by the processor 34. It receives and process data from the various sensors (pH, optical density, temperature, pressure), and coordinates the activity of the solenoids, pumps, steam cleaning, lighting and heating. If desired, the processor 34 can be made to interface wirelessly to a computer to allow remote monitoring and control.

Figure 5A:
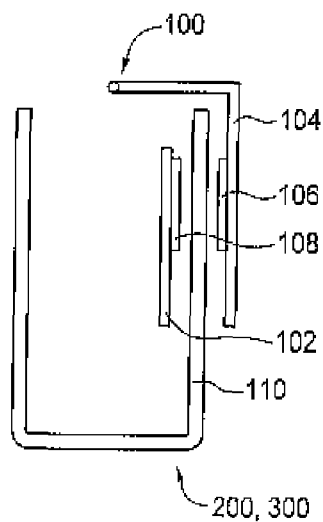
FIGS. 5A and 5B are longitudinal sectionals view of the cleaner and the alternative cleaner.
Figure 5B:
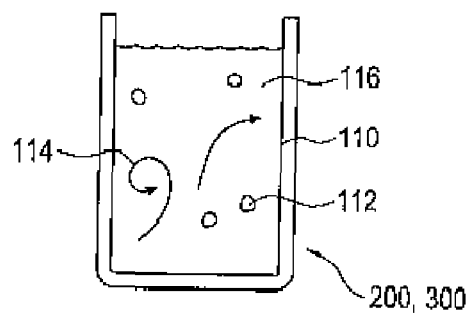

As shown in FIG. 5A, a cleaner, generally referred to as 100 is for placing in the scale up and feed culture vessels 200, 300. A blade 102 for locating inside the culture vessels 200, 300 is magnetically coupled to a rotating arm 104 which is configured to move around the outside of the vessels 200, 300. As would be known to one skilled in the art, the magnet 106 and the magnetic material 108 can be interchangeably located on the rotating arm 104 and the blade 102. Alternatively, the blade 102 may be directly driven. The cleaner 100 is preferably contoured to the inner surface 110 of the vessel 200, 300, or can be flexible, for example, but not limited to iron filings encased in a long flexible plastic covering or brushes located on the blade 102. In an alternative embodiment, as shown in FIG. 5B, small free floating parts 112 are placed inside the culture vessels 200, 300. These free floating parts 112 are carried by gas currents 114 in the culture medium 116 and keep the inner surface 110 clean through continuous small impacts.

Method:

The design of the bioreactor provides for a minimum downtime and maximum efficiency. As each vessel is emptied, both the vessel and the lines leading to it can be sterilized. Additionally, the entire bioreactor can be cleaned and sterilized. Once scale up has begun, the system is closed and remains closed until harvest, which is preferably in late log phase, but may be earlier or later. In this closed system (i.e. one that does not require open transfers), the volume of the vessels increases incrementally from the seed vessel to the scale up vessel to the feed vessel, on a schedule and under control of the processor, hence contamination can be contained to a relatively small volume, as compared to having one large culture vessel filled with culture medium. Also, the level of security increases as the number of valves, lines and vessels from the ambient environment increase, hence the larger the vessel, the further it is removed from ambient and therefore the less chance there is of contamination. Culture medium used for cleaning the vessels may be dumped or retained to scale up the culture volume. Should contamination occur in any one vessel the processor will detect the contamination, based on data from at least one sensor and will control emptying of the vessel. The vessel may additionally be cleaned, by the processor signaling a cleaning step before the sterilizing cycle begins. Gaseous sterilizant is fed through the bioreactor by means of the steam lines and manifold. All transfers are automated, thereby reducing the risk of contamination.

Second Embodiment

Itemized list of the main components:
1. Sterilizant system;
2. Water treatment system;
3. Clean-in-place system (CIP);
4. Air and CO2 addition;
5. Control system—Programmable Logic Controller (PLC) Based;
6. Seed culture container;
7. Feed culture vessel; and
8. Cooling system.

Figure 7:
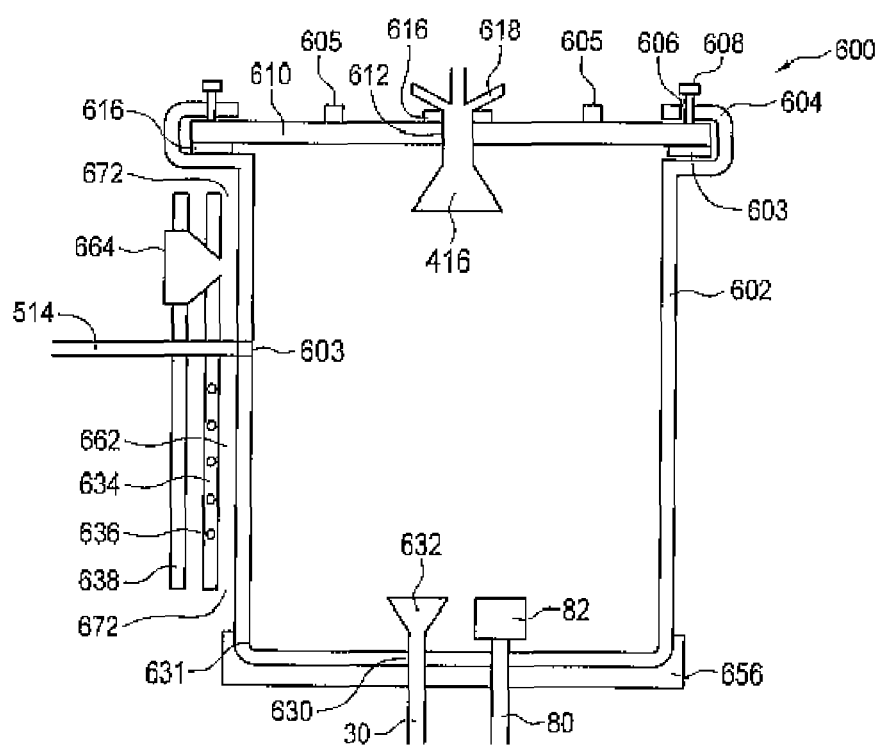
FIG. 7 is a longitudinal sectional view of the feed culture vessel of the bioreactor of FIG. 6.

FIG. 7 is a schematic of a second embodiment of a bioreactor 510. The seed culture container 512 connects via the first culture line 514 to a feed vessel 600. The seed culture container 512 is transiently attached to the first culture line 514, which directly feeds the feed vessel 600. The first culture line 514 enters the feed vessel 600 at an inlet 603. The first culture line 514 has a two way valve 48 in line.

The air line 516 and the first culture line 514 enter the seed culture container 512 through a bung 518. The air line 516 is connected to a pump 520 for pumping air into the carboy 512, thereby increasing the pressure, and forcing culture through the first culture line 514. The air line 516, first culture line 514, bung 518 and pump 520 are collectively referred to as the pressure driven transfer system. A steam generator 24 is used for sterilizing the bioreactor 510. An air source 26, which may be a tank or ambient air and a pressurized CO2 tank 28 are attached via gas lines 30 to the injectors 32 located in the interior 601 of the feed vessel 600. A processor 34 controls delivery of air and CO2 as needed. A regulator and digital pressure gauge 36 is located downstream from the CO2 tank 28 on the CO2 line 38 portion of the gas line 30. A valve 31 is located downstream. A three way, 2 position solenoid valve 40 communicates with the processor 34 and is located on the gas lines 30. An air pump 42 is on the air line 44 portion of the gas line 30 and is calibrated to produce a pressure of about 2 psi to about 15 psi. Check valves 46 are located on the air line 44 both on the air intake line and the air pump line. A 0.1 μm steam-in-place filter 48 is located upstream from the solenoid valve 40. It splits the air line 44 into an air dump line 50 and the air line 44. The CO2 line 38 and the air line 44 connect at three way solenoid valves 40 to form the gas lines 30. The CO2 line 38, the air line 44, and the gas lines 30 form a manifold. This manifold also distributes steam or more generally, sterilizant, allowing for easy steam sterilization of the lines.

A water line 390 for sea water has an inline 100 μm filter 392, and a valve 393. It is joined by two nutrient lines 394 from nutrient packs 396 to become a culture medium line 398. Each nutrient line 394 is equipped with a pump 408, which is preferably a peristaltic pump or shuttle pump, but may be a rotary pump and a check valve 410. The nutrient lines 394 upstream from the peristaltic pump 408 are preferably disposable. The culture medium line 398 passes through an inline pump 408, which is preferably a peristaltic pump or shuttle pump, but may be a rotary pump. A sprayer 416 sprays the contents of the line into the feed vessel 600. The sprayer 416 is preferably a rotary spray nozzle. This is the CIP. The feed vessel 600 has a pressure relief line 700 with a pressure relief valve 702 and an atmosphere dump 704.

A fresh water supply 430 passes through a 50 μm filter 432 and enters a steam generator, for example, a boiler 434. A first steam line 436 from the steam generator 434 enters the air line 44 between the filter 48 and the solenoid valves 40. A second steam line 438 enters the water line upstream from the nutrient lines 394. The steam lines, manifold and overall integration of the bioreactor allow for in situ sterilization of either the entire bioreactor, or select vessels and lines. The steam lines 436, 438 have a pressure release valve 439.

A third culture line 80 leaves the feed culture vessel 600 through an outlet 82. The third culture line 80 passes through an inline pump 84, which is preferably a peristaltic pump or a shuttle pump, but may be a rotary pump, and a second dump line 86 splits off. Both have two way valves—88 on the dump line 86 and 90 on the third culture line 80. Additionally, the third culture line 80 has a one way check valve 92 downstream. An outlet 94 terminates the third culture line 80. At this point the feed culture is supplied to the customer either as is, or in a concentrated form, by including a concentrator 96 either upstream or downstream from the outlet 94. The concentrator 96 may be any suitable concentrator, for example, but not limited to a centrifuge or a filtration system.

The feed culture vessel, generally referred to as 600, is shown in FIG. 7. The feed culture vessel is about 100 to about 100,000 liters, or about 250 to about 75,000 liters or 50,000 liters and all ranges therebetween. If algae or other plant material is to be cultured, at least the side walls 602 are transparent or light transmitting. The side wall 602 is preferably polycarbonate. The lip 603 of the wall 602 is formed into a flange 604 and has openings 606 to accept bolts 608 for affixing an airtight lid 610. As the vessel is steam-cleaned, both the vessel 600 and the lid 610 are made of steam-resistant material, for example, but not limited to fiberglass or a heat resistant polyethylene such as Tyvar®. The lid 610 has an access port 612 for accepting a clean in place system (CIP), generally referred to as 416. Gaskets 616 are located between the lid 610 and flange 604 and between a CIP flange 618 and the lid 610.

Figure 6:
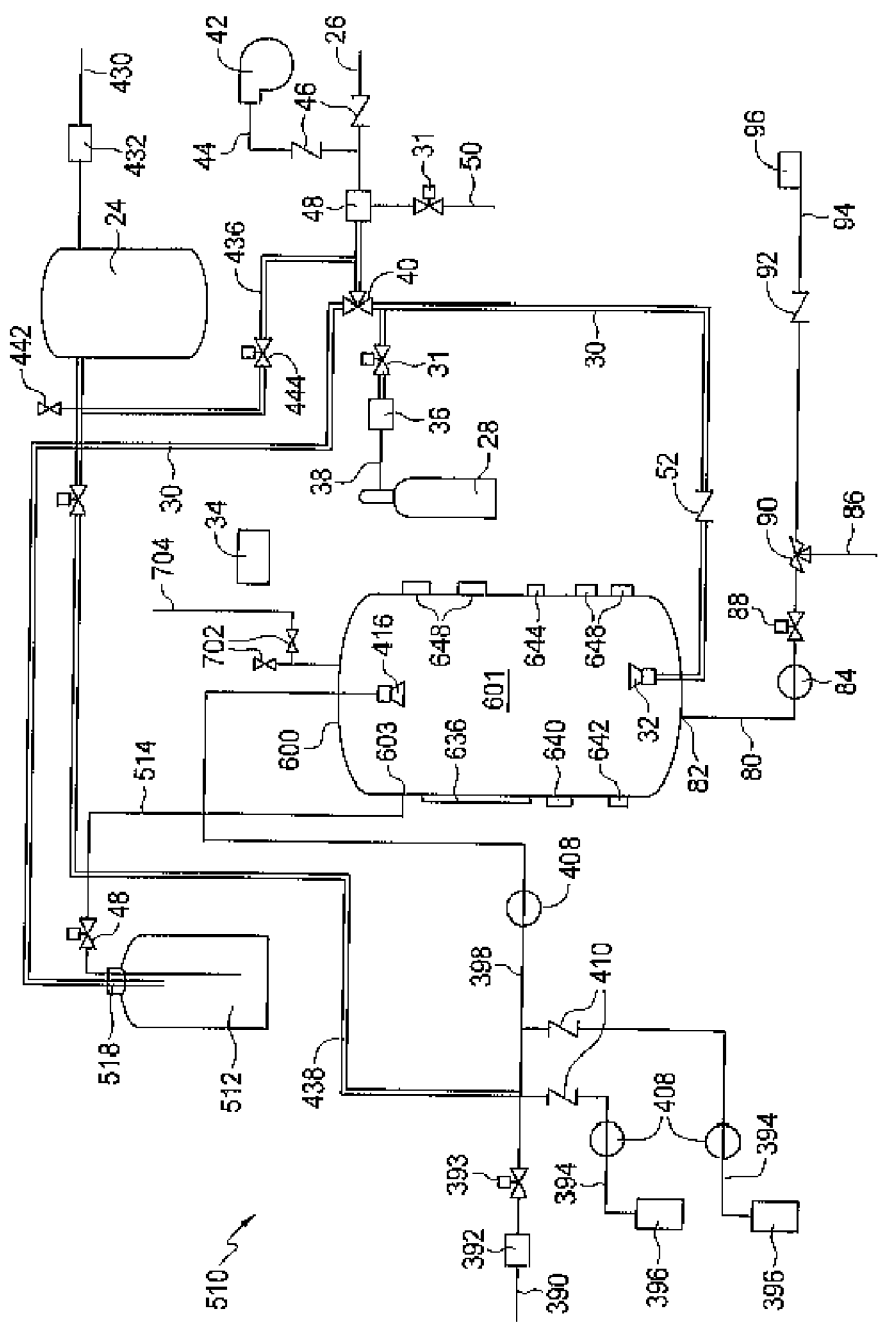
FIG. 6 is a schematic of a second embodiment.

The feed culture vessel 600 is equipped with a bottom access 630 on or in the vicinity of the bottom 631 connected to the gas lines 30 and an outlet 82 connected to the third culture line 80. The gas line 30 terminates in a sparger 632. The first culture line 514 enters the feed vessel 600 at an inlet 603. An optional thin plastic polymer shell 634 surrounds the vessel 600 and is equipped with light emitting diode grow lights 636. Lights 605 may additionally be provided on the lid 610. An optional reflective surface 638 is located on an outer side of the shell 634. As shown in FIG. 6, the feed culture vessel 600 is provided with sensors for reporting culture conditions, for example, but not limited to each of a pH 640, optical density 642, temperature 644, and pressure sensor 646. Capacitance sensors 648 are located at a number of depths, for example, two located at ⅓ and ⅔ depth, three located at ¼, ½, ¾ depth or four located at ⅕, ⅖, ⅗ and ⅘ depth.

Figure 8:
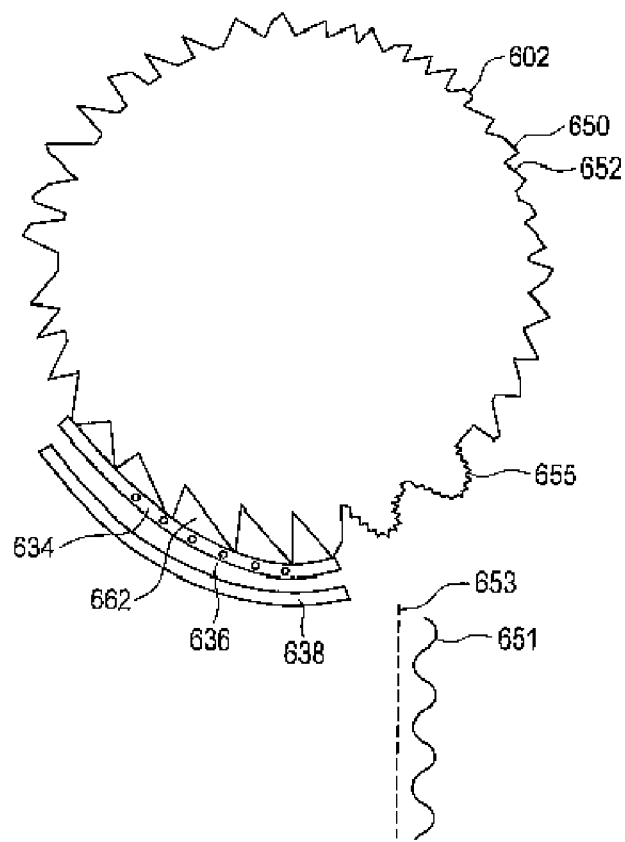
FIG. 8 shows the side wall of the feed culture vessel of FIG. 7.

As shown in FIG. 8, the side wall 602 is formed into vertically disposed ridges 650 and valleys 652. They may be rounded or sharp edged and may be wavy 651 about their vertical axis 653. The vertical contours 654 may be, but are not limited to waves, or ridges and valleys, or peaks and troughs or are accordion-shaped, and are substantially vertical, for example, the vertical axis is normal to the floor, about 85 degrees relative to the floor, about 80 degrees relative to the floor or about 75 degrees relative to the floor. The vertical contours 654 function to increase the surface area of the side wall 602 and thereby increase light penetration in the feed culture vessel 600. The peak to valley height of the contours 654 is about 1/16 of an inch to about 1 foot, or about 1 inch to about 6 inches or about 3 inches and all ranges therebetween. The distance between the peaks is about 1/16 of an inch to about 1 foot, or about 1 inch to about 6 inches, or 3 inches and all ranges therebetween. Additionally, the contours 654 preferably have small corrugations 655 to further increase the surface area. A bottom plate 656 retains the side wall 602 and has plate contours 658 that correspond to the contours 654 of the side wall 602. Alternatively, the bottom plate 656 may have a contoured groove 660 (shown in FIG. 8, inset) to accept the side wall 602.

A cooling system provides air flow to the space between the feed culture vessel 600 and light emitting diode grow lights 636 (See FIG. 8). This space is referred to as the air channel 662. As shown in FIG. 7, blowers or fans 664 force air down through the air channels 662, which then exits from the bottom 672 of the air channels 662. Similarly, blowers or fans force air down through the air channels in the vessels of FIG. 3 and FIG. 4.

The bioreactor is controlled by the processor 34. It receives and process data from the various sensors (pH, optical density, temperature, pressure), and coordinates the activity of the solenoids, pumps, steam cleaning, lighting and heating. If desired, the processor 34 can be made to interface wirelessly to a computer to allow remote monitoring and control.

The cleaner and alternative cleaner are shown in FIGS. 5 and 6.

Method:

The design of the bioreactor provides for a minimum downtime and maximum efficiency. As the vessel is emptied, both the vessel and the lines leading to it can be sterilized. Additionally, the entire bioreactor can be cleaned and sterilized. Once scale up has begun, the system is closed and remains closed until harvest, which is preferably in late log phase, but may be earlier or later. Initially, the feed culture vessel contains a small amount of culture medium. In this closed system (i.e. one that does not require open transfers), the volume of culture medium increases incrementally on a schedule, under control of the processor, hence contamination has a smaller chance of establishing itself. Since less medium (a vector for contamination) is added at the beginning of the scale up, there is a smaller chance that contaminant organisms are added early on. This limits the amount of time that contaminants are multiplying in the system, and increases competition for resources, which on average will produce significantly less contaminated cultures. Culture medium used for cleaning the vessels may be dumped or retained to scale up the culture volume. Should contamination occur in the vessel the processor will detect the contamination, based on data from at least one sensor and will control emptying of the vessel. The vessel may additionally be cleaned by the processor signaling a cleaning step before the sterilizing cycle begins. Gaseous sterilizant is fed through the bioreactor by means of the steam lines and manifold.

Third Embodiment

Itemized List of the Main Components:
1. Sterilizant system;
2. Water treatment system;
3. Clean-in-place system (CIP);
4. Air and CO2 addition;
5. Control system—Programmable Logic Controller (PLC) Based;
6. Seed culture container;
7. Culture vessel; and
8. Cooling system.

Figure 9:
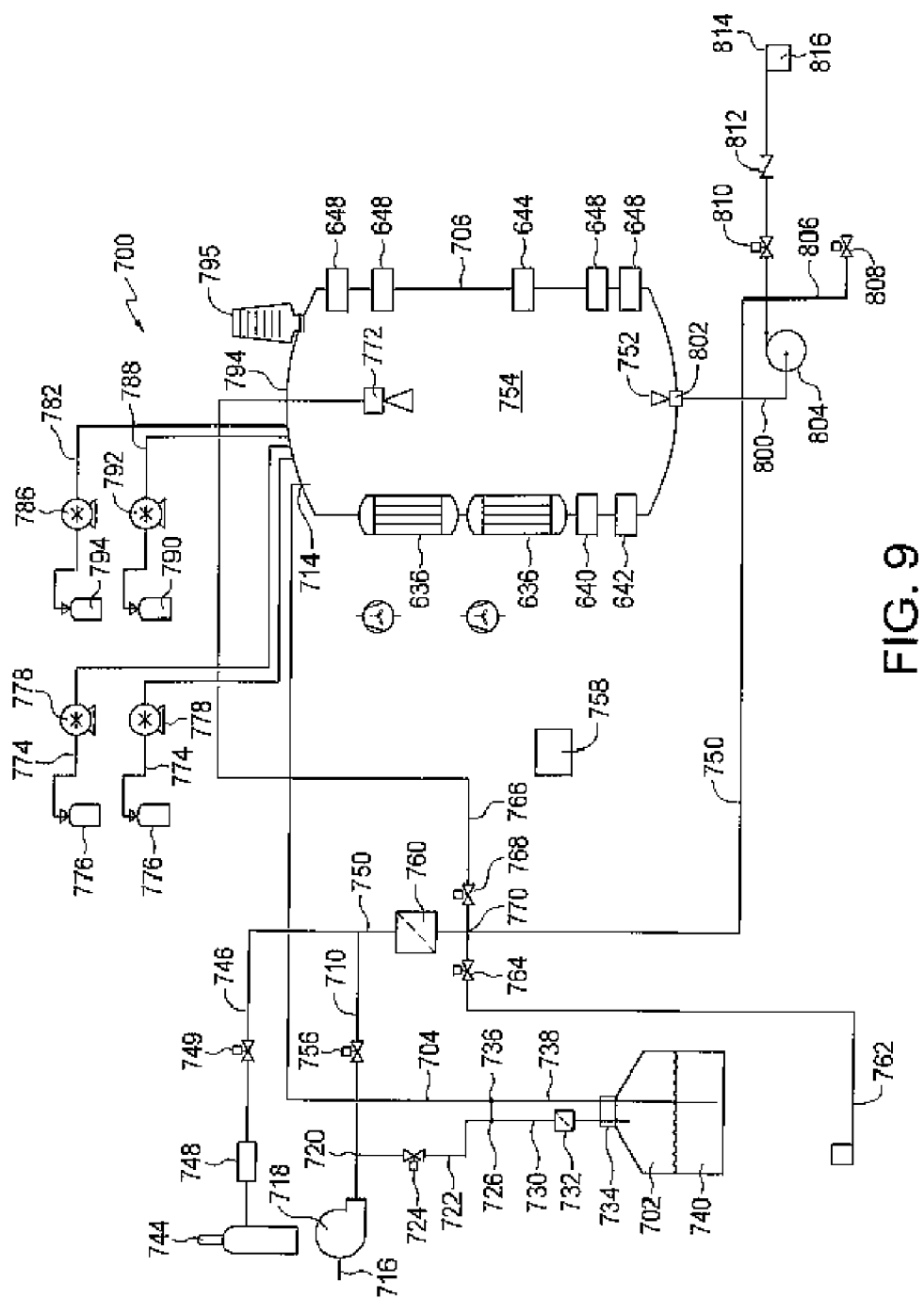
FIG. 9 is a schematic of the third embodiment of a bioreactor.

A schematic of a third embodiment, generally referred to as 700 is shown in FIG. 9. The seed culture container 702 connects via the first culture line 704 to the culture vessel 706. The seed culture container 702 is transiently attached to a first culture line 704, which directly feeds the culture vessel 706. The first culture line 704 enters the culture vessel 706 at an inlet 714.

A first air line 710 has an air source 716 which may be a tank or ambient air. A pump 718 forces the air to a T-junction 720, to a second air line 722 that branches from the first air line 710 at the T-junction 720. The pump 718 is calibrated to produce a pressure of about 2 psi to about 15 psi. The second air line 722 has a two way manual valve 724 and a fitting 726 downstream from the valve 724 for a user to attach a third air line 730 with an air filter 732. The third air line 730 enters the seed culture container 702 through a bung 734. The first culture line 704 similarly has a fitting 736 for attaching a second culture line 738 that enters the seed culture container 702 through the bung 734. When the valve 724 is open and the air lines 706, 722, 730 are pressurized by the pump 718, culture 740 is forced from the seed culture container 702 to the first culture line 704 that leads to the culture vessel 706. The air lines 706, 722, 730, culture line 704, 738 and pump 718 are collectively referred to as the pressure driven transfer system. Alternatively, the transfer valve 22 described above could be employed.

A pressurized CO2 tank 744 provides CO2 to a CO2 line 746. A regulator and digital pressure gauge 748 is located downstream from the CO2 tank 744 on the CO2 line 746 and a three way two position solenoid valve 749 is located downstream from the regulator and digital pressure gauge 748. The CO2 line 746 joins the first air line 710 to form a gas line 750, which delivers to the culture vessel 706 through injectors or spargers 752 located in the interior 754 of the culture vessel 706. Upstream from the gas line 750, a three way, two position solenoid valve 756 is located on the first air line 710. A processor 758 controls delivery of air and CO2 as needed by communicating with the valves 746, 756. A 0.1 μm filter 760 is located on the gas line 750.

A water line 762 for sea water has a two position solenoid valve 764 and optionally, an inline ultraviolet filter. The water line 762 and the gas line 750 connect to form a common line 766 downstream of the valve 764. A two position solenoid valve 768 is downstream from the connection 770. The common line 766 enters the culture vessel 706 at a sprayer 772 that sprays the contents of the common line 766 (which is normally primarily liquid, but, by closing the valve 726 on the water line 762, can become a gas line) into the culture vessel 706. The sprayer 772 is preferably a rotary spray nozzle.

Two nutrient lines 774 from nutrient packs 776 are each equipped with a pump 778, which is preferably a peristaltic pump or shuttle pump, but may be a rotary pump. The nutrient lines 774 upstream from the peristaltic pump 778 are preferably disposable. The nutrient lines 774 enter the culture vessel 706 at an upper end 780.

A sterilizant line 782 from a sterilizer pack 784 is equipped with a pump 786, which is preferably a peristaltic pump or shuttle pump, but may be a rotary pump. Similarly, a neutralizer or detoxifier line 788 from a neutralizer or detoxifier pack 790 is equipped with a pump 792. The lines 782, 788 enter the culture vessel 706 at an upper end 794. The gas line 750, common line 766 and sterilizant line 782 form a manifold to provide an integrated sterilization system for in situ sterilization.

A 2-directional air filter 795 extends from the culture vessel 706 at an upper end 794 and functions as a pressure release valve. A third culture line 800 leaves the culture vessel 706 through an outlet 802. The third culture line 800 passes through an inline pump 804, which is preferably a peristaltic pump or a shuttle pump, but may be a rotary pump, and a dump line 806 splits off. Both have two way valves—808 on the dump line 806 and 810 on the third culture line 800. Additionally, the third culture line 800 has a one way check valve 812 downstream. An outlet 814 terminates the third culture line 800. At this point the feed culture is supplied to the customer either as is, or in a concentrated form, by including a concentrator 816 either upstream or downstream from the outlet 802. The concentrator 816 may be any suitable concentrator, for example, but not limited to a centrifuge or a filtration system.

A liquid sterilizer pack 784 contains sterilizant that is used for sterilizing the bioreactor 700. The sterilizant may be a weak sodium hypochlorite solution, for example, 1% in water. The neutralizer or detoxifier may be a de-chlorinator. The path of the sterilizant is as follows:

Sterilizant leaves sterilizant pack 784 and travels through sterilizant line 782, under pressure resulting from the pump 786 to the culture vessel 706 where it is sprayed into the culture vessel 706 with the sprayer 772 (the CIP system). The sterilizant leaves the culture vessel 706 through the injector 752 and travels through the gas line 750 to the connection 770, into the common line 766, through open valve 768. It is stopped by the filter 760 and the valve 762, which is closed. It then re-enters the culture vessel 706 through the sprayer 772, forming an integrated sterilization system for in situ sterilization. Once sterilization is completed, the system is neutralized by the neutralizer. The neutralizer leaves the neutralizer pack 776 and travels through neutralizer line 788, under pressure resulting from the pump 792 to the culture vessel 706 where it is sprayed into the culture vessel 706 with the sprayer 772 (the CIP system). The neutralizer leaves the culture vessel 706 through the injector 752 and travels through the gas line 750 to the connection 770, into the common line 766, through open valve 768. It is stopped by the filter 760 and the valve 762, which is closed. It then re-enters the culture vessel 706 through the sprayer 772, forming a closed neutralization loop.

The culture vessel, generally referred to as 706, is the same of that of FIG. 7 (where the culture vessel is generally referred to as 600). The culture vessel is about 100 to about 100,000 liters, or about 250 to about 75,000 liters or 50,000 liters and all ranges therebetween. If algae or other plant material is to be cultured, at least the side walls 602 are transparent or light transmitting. The side wall 602 is preferably polycarbonate, but may be acrylic or glass. The lip of the wall 602 is formed into a flange 604 and has openings 606 to accept bolts 608 for affixing an airtight lid 610. As the vessel is steam-cleaned, both the vessel 600 and the lid 610 are made of steam-resistant material, for example, but not limited to fiberglass or a heat resistant polyethylene such as Tyvar®. The lid 610 has an access port 612 for accepting a clean in place system (CIP), generally referred to as 416. Gaskets 616 are located between the lid 610 and flange 604 and between a CIP flange 218 and the lid 610. An optional thin plastic polymer shell 634 surrounds the vessel 600 and is equipped with light emitting diode grow lights 636. An optional reflective surface 638 is located on an outer side of the shell 634. The culture vessel 706 is provided with sensors for reporting culture conditions, for example, but not limited to each of a pH 640, optical density 642, temperature 644, and pressure sensor 646. Capacitance sensors 648 are located at a number of depths, for example, two located at ⅓ and ⅔ depth, three located at ¼, ½, ¾ depth or four located at ⅕, ⅖, ⅗ and ⅘ depth.

As shown in FIG. 8, the side wall 602 is formed into vertically disposed ridges 650 and valleys 652. They may be rounded or sharp edged and may be wavy 651 about their vertical axis 653. The vertical contours 654 may be, but are not limited to waves, or ridges and valleys, or peaks and troughs or are accordion-shaped, and are substantially vertical, for example, the vertical axis is normal to the floor, about 85 degrees relative to the floor, about 80 degrees relative to the floor or about 75 degrees relative to the floor. The vertical contours 654 function to increase the surface area of the side wall 602 and thereby increase light penetration in the feed culture vessel 600. The peak to valley height of the contours 654 is about 1/16 of an inch to about 1 foot, or about 1 inch to about 6 inches or about 3 inches and all ranges therebetween. The distance between the peaks is about 1/16 of an inch to about 1 foot, or about 1 inch to about 6 inches, or about 3 inches, and all ranges therebetween. Additionally, the contours 654 preferably have small corrugations 655 to further increase the surface area. As shown in FIG. 7 a bottom plate 656 retains the side wall 602 and has plate contours 658 that correspond to the contours 654 of the side wall 602. Alternatively, the bottom plate 656 may have a contoured groove to accept the side wall 602.

A cooling system provides air flow to the space between the feed culture vessel 600 and light emitting diode grow lights 636 (See FIG. 8). This space is referred to as the air channel 662. As shown in FIG. 7, a series of blowers or fans 664 forces air through the air channels 662, which then exits from the bottom 672 of the air channels 662 (see FIG. 7).

The bioreactor is controlled by the processor 758. It receives and process data from the various sensors (pH, optical density, temperature, pressure), and coordinates the activity of the solenoids, pumps, cleaning, sterilizing, neutralizing, lighting and heating. If desired, the processor 758 can be made to interface wirelessly to a computer to allow remote monitoring and control.

The cleaner and alternative cleaner are shown in FIGS. 5A and 5B.

Figure 10:
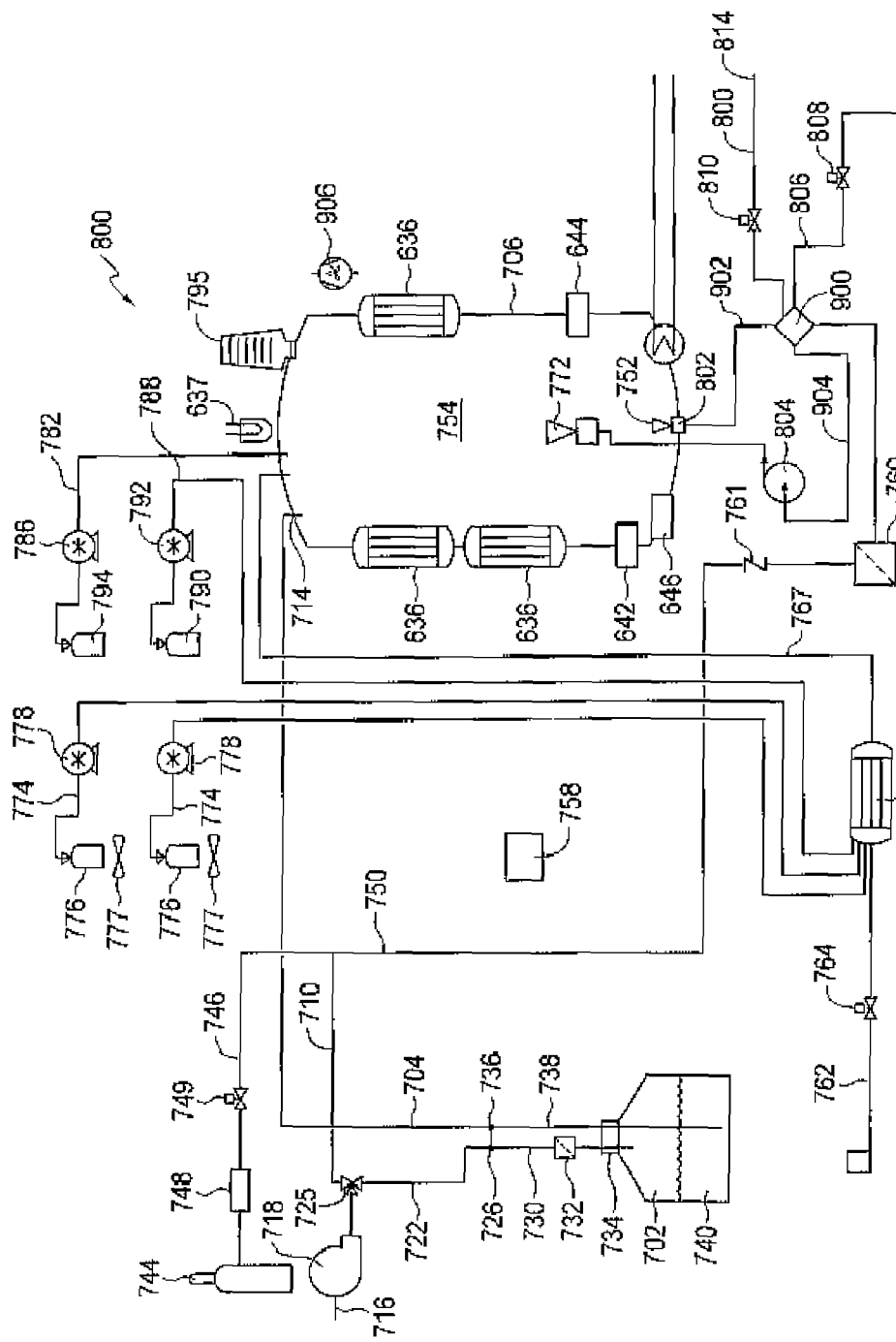
FIG. 10 is a schematic of the fourth embodiment of a bioreactor.

A schematic of a fourth embodiment, generally referred to as 800 is shown in FIG. 10. The seed culture container 702 connects via the first culture line 704 to the culture vessel 706. The seed culture container 702 is transiently attached to a first culture line 704, which directly feeds the culture vessel 706. The first culture line 704 enters the culture vessel 706 at an inlet 714.

A first air line 710 has an air source 716 which may be a tank or ambient air. A pump 718 forces the air to a three way valve 725, to a second air line 722 that branches from the first air line 710 at the three way valve 725. The pump 718 is calibrated to produce a pressure of about 2 psi to about 15 psi. The second air line 722 has a fitting 726 downstream from the valve 725 for a user to attach a third air line. An air filter 732 is downstream from this. The second air line 722 enters the seed culture container 702 through a bung 734. The first culture line 704 similarly has a fitting 736 for attaching a second culture line 738 that enters the seed culture container 702 through the bung 734. When the valve 725 is open and the air lines 706, 722 are pressurized by the pump 718, culture 740 is forced from the seed culture container 702 to the first culture line 704 that leads to the culture vessel 706. The air lines 706, 722, culture line 704, 738 and pump 718 are collectively referred to as the pressure driven transfer system. Alternatively, the transfer valve 22 described above could be employed.

A pressurized CO2 tank 744 provides CO2 to a CO2 line 746. A regulator and digital pressure gauge 748 is located downstream from the CO2 tank 744 on the CO2 line 746 and a three way two position solenoid valve 749 is located downstream from the regulator and digital pressure gauge 748. A processor 758 controls delivery of air and CO2 as needed by communicating with the valve 749. A one way valve 761 is upstream from a 0.1 μm filter 760 on the gas line 750. The CO2 line 746 joins the first air line 710 to form a gas line 750. The gas line 750 enters a manifold 900 from which a delivery line 902 passes through a pump 804 to a sprayer, sparger or injector 772 located in the interior 754 of the culture vessel 706. The sprayer 772 is preferably a rotary spray nozzle. The pump 804 is preferably a peristaltic pump or a shuttle pump, but may be a rotary pump, A water line 762 for sea water has a two position solenoid valve 764 and an inline ultraviolet filter 763. The water line 762, nutrient lines 774 and sterilizant line 782 connect to form a common line 767 downstream of the valve 764 and upstream of the ultraviolet filter 763. The common line 766 enters the culture vessel 706.

The two nutrient lines 774 from nutrient packs 776 are each equipped with a pump 778, which is preferably a peristaltic pump or shuttle pump, but may be a rotary pump. The nutrient lines 774 upstream from the peristaltic pump 778 are preferably disposable. The nutrient lines 774 enter the culture vessel 706 at an upper end 780. A stir motor 777 is located below the nutrient packs 776 to keep the nutrients stirred.

A sterilizant line 782 from a sterilizer pack 784 is equipped with a pump 786, which is preferably a peristaltic pump or shuttle pump, but may be a rotary pump. Similarly, a neutralizer or detoxifier line 788 from a neutralizer or detoxifier pack 790 is equipped with a pump 792. The lines 782, 788 enter the culture vessel 706 at an upper end 794.

The liquid sterilizer pack 784 contains sterilizant that is used for sterilizing the bioreactor 700. The sterilizant may be a weak sodium hypochlorite solution, for example, 1% in water. The neutralizer or detoxifier may be a de-chlorinator.

A 2-directional air filter 795 extends from the culture vessel 706 at an upper end 794 and functions as a pressure release valve. A common line 902 leaves the culture vessel 706 through an outlet 752 located at an aperture 802. The common line 902 passes through the manifold 900 and a dump line 806 and a third culture line 800 splits off. Both have two way valves—808 on the dump line 806 and 810 on the third culture line 800. An outlet 814 terminates the third culture line 800.

The culture vessel, generally referred to as 754, is the same of that of FIG. 7 (where the culture vessel is generally referred to as 600). The vessel 754 is equipped with light emitting diode grow lights 637 and banks of fluorescent lights 636. An optional reflective surface 638 is located on an outer side of the shell 634. The culture vessel 706 is provided with sensors for reporting culture conditions, for example, but not limited to each of an optical density 642, temperature 644, and pressure sensor 646. Fans 906 are used to cool the air surrounding the vessel 754. A cooling heat exchanger 16 as shown in FIG. 1, is used to cool the vessel 754.

As shown in FIG. 8, the side wall 602 is formed into vertically disposed ridges 650 and valleys 652. They may be rounded or sharp edged and may be wavy 651 about their vertical axis 653. The vertical contours 654 may be, but are not limited to waves, or ridges and valleys, or peaks and troughs or are accordion-shaped, and are substantially vertical, for example, the vertical axis is normal to the floor, about 85 degrees relative to the floor, about 80 degrees relative to the floor or about 75 degrees relative to the floor. The vertical contours 654 function to increase the surface area of the side wall 602 and thereby increase light penetration in the feed culture vessel 600. The peak to valley height of the contours 654 is about 1/16 of an inch to about 1 foot, or about 1 inch to about 6 inches or about 3 inches and all ranges therebetween. The distance between the peaks is about 1/16 of an inch to about 1 foot, or about 1 inch to about 6 inches, or about 3 inches, and all ranges therebetween. Additionally, the contours 654 preferably have small corrugations 655 to further increase the surface area. As shown in FIG. 7 a bottom plate 656 retains the side wall 602 and has plate contours 658 that correspond to the contours 654 of the side wall 602. Alternatively, the bottom plate 656 may have a contoured groove to accept the side wall 602.

A cooling system provides air flow to the space between the feed culture vessel 600 and light emitting diode grow lights 636 (See FIG. 8). This space is referred to as the air channel 662. As shown in FIG. 7, a series of blowers or fans 664 forces air through the air channels 662, which then exits from the bottom 672 of the air channels 662 (see FIG. 7).

The bioreactor is controlled by the processor 758. It receives and process data from the various sensors (pH, optical density, temperature, pressure), and coordinates the activity of the solenoids, pumps, cleaning, sterilizing, neutralizing, lighting and heating. If desired, the processor 758 can be made to interface wirelessly to a computer to allow remote monitoring and control.

Method:

The design of the bioreactor provides for a minimum downtime and maximum efficiency. As the vessel is emptied, both the vessel and the lines leading to it can be sterilized. Additionally, the entire bioreactor can be cleaned and sterilized. Once scale up has begun, the system is closed and remains closed until harvest, which is preferably in late log phase, but may be earlier or later. Initially, the feed culture vessel contains a small amount of culture medium. In this closed system (i.e. one that does not require open transfers), the volume of culture medium increases incrementally on a schedule, under control of the processor, hence contamination can be contained to a relatively small volume. Since less medium (a vector for contamination) is added at the beginning of the scale up, there is a smaller chance that contaminant organisms are added early on. This limits the amount of time that contaminants are multiplying in the system, and increases competition for resources, which on average will produce significantly less contaminated cultures. Culture medium used for cleaning the vessels may be dumped or retained to scale up the culture volume. Should contamination occur in the vessel the processor will detect the contamination, based on data from at least one sensor and will control emptying of the vessel. The vessel may additionally be cleaned by the processor signaling a cleaning step before the sterilizing cycle begins. Liquid sterilizant is fed through the bioreactor by means of a closed loop recirculating system.

All methods described herein can be performed in any suitable order unless otherwise indicated herein or otherwise clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Advantages of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive. It is understood that numerous other modifications and variations can be devised without departing from the scope of the example embodiment. For example, a heat exchanger could be integrated into the cooling system, filtering of the water entering the integrated system can be done using inline filters on each integrated system, or using a larger rotating drum or rotary screen micron filter to filter water for a number of integrated systems. The pore sizes of the filters are approximate sizes, for example, a 0.1 μm filter may be about 0.05 μm to about 0.15 μm, a 1 μm filter may be about 0.5 to about 1.5 μm, a 50 μm filter may be about 25 μm to about 75 μm, and a 100 μm filter may be about 75 μm to about 150 μm, or about 75 μm to about 125 μm and all ranges therebetween. Filtration may be combined with other known methods to remove or kill contaminants, whether algae, plankton, or bacteria or may be replaced with other methods. UV filtering can be done using one large filter for numerous integrated systems, or in our case integrating an individual UV filter with each integrated system. As would be known to one skilled in the art, sterilization may be effected by sterilizants other than steam and therefore the steam generator and various lines may be replaced with chemical tanks, for example, but not limited to tanks of ethylene oxide or ozone. The bioreactor may be used for fresh water, salt water, brine, brackish water and any other liquid that can be used as the fluid in bioreactor cultures. Algal cultures include isochrysis, nannochloropsis, pavlova, tetraselmis, or any of the variety of industry standard species. Mixed culture includes a nannochloropsis to rotifer production system, or a nannochloropsis and isochrysis to rotifer production system. It can also be used as a fermenter. The nutrient packs may contain a carbohydrate source, such as glucose. Should contamination be a recurring problem, an additional vessel can be added to the system having a volume that is larger than the preceding vessel and smaller than the next vessel, in other words, having an incremental volume increase. While the described embodiments have one or two permanent vessels, a series of vessels ranging from three, to four, to five or more vessels is contemplated. A number of spargers may be employed to ensure proper mixing. This is especially relevant in the alternative embodiment when the depth of the valleys increases. As would be known to one skilled in the art, components described in one embodiment may be used in the other embodiments. The processor may be programmed to incrementally increase culture volume on a cell density based schedule or on a time schedule.

The invention claimed is:

1. A bioreactor, the bioreactor including a vessel comprising: a light transmitting side wall, wherein the side wall includes a plurality of substantially vertical peaks and valleys wherein a peak to valley height is about 1 inch to about 6 inches and the distance between the peaks is about 1 inch to about 6 inches; a plurality of vertically disposed lights proximate an outer surface of the side wall; a reflective layer proximate the lights, the plurality of peaks and valleys and the reflective layer defining a plurality of air channels; a lid; a bottom, the side wall, lid and bottom defining an interior; a base, the base contoured to mate with the side wall; a plurality of sensors for reporting culture conditions; a gas sparger in the interior for communication with a gas line; a culture medium sprayer for communication with a culture medium line; a culture inlet and a culture outlet and a combined stand and cooling system, the combined stand and cooling system comprising a framework of conduits and an at least one blower, the blower in gaseous communication with a conduit inlet, the frame work of conduits having a series of outlets aligned with the air channels, such that in use, air is blown into a lower end of each of the plurality of air channels and rises to a top end of each the plurality of air channels thereby cooling the bioreactor vessel.

2. A bioreactor vessel, the vessel comprising: a light transmitting side wall, wherein the side wall includes a plurality of substantially vertical peaks and valleys; a shell proximate an outer surface of the side wall and abutting the peaks; a plurality of vertically disposed lights mounted on the shell; the plurality of peaks and valleys and the shell defining a plurality of air channels; a lid; a bottom, the side wall, lid and bottom defining an interior; a base, the base contoured to mate with the side wall; a plurality of sensors for reporting culture conditions; a gas sparger in the interior for communication with a gas line; a rotary culture medium sprayer for communication with a culture medium line; a culture inlet and a culture outlet; and a combined stand and cooling system for use with a blower, the combined stand and cooling system comprising a framework of conduits, a conduit inlet for gaseous communication with the blower, the frame work of conduits having a series of outlets aligned with the air channels, such that in use, air is blown into a lower end of each of the plurality of air channels and rises to a top end of each the plurality of air channels thereby cooling the bioreactor vessel.

3. The bioreactor vessel of claim 2, further comprising the blower, the blower in gaseous communication with the conduit inlet.

4. The bioreactor vessel of claim 3, wherein the peaks and valleys includes waves normal to the peaks and valleys.

5. A bioreactor vessel, the vessel comprising: a light transmitting side wall, wherein the side wall includes a plurality of substantially vertical peaks and valleys; the side wall includes a plurality of substantially vertical peaks and valleys; a shell proximate an outer surface of the side wall and abutting the peaks; a plurality of vertically disposed lights mounted on the shell; the plurality of peaks and valleys and the shell defining a plurality of air channels; a lid; a bottom, the side wall, lid and bottom defining an interior; a base, the base contoured to mate with the side wall; a plurality of sensors for reporting culture conditions; a gas sparger in the interior for communication with a gas line; a culture medium sprayer for communication with a culture medium line; a culture inlet and a culture outlet; and a cooling system, the cooling system comprising an at least one fan and a distribution plate in communication with the at least one fan, the distribution plate having a network for directing air flow into each of the plurality of air channels.

6. The bioreactor vessel of claim 5, wherein the culture medium sprayer is a rotary culture medium sprayer.

7. The bioreactor vessel of claim 6, wherein the peaks and valleys includes waves normal to the peaks and valleys.

8. The bioreactor vessel of claim 5, further comprising a cooling plate disposed beneath the distribution plate and for communication with a refrigeration source.

* * * * *